(12) United States Patent
Paik et al.

(10) Patent No.: US 8,198,038 B2
(45) Date of Patent: Jun. 12, 2012

(54) PLASMA BIOMARKER TOOL FOR THE DIAGNOSIS OF LIVER CANCER COMPRISING LIVER CARBOXYLESTERASE 1 AND LIVER CANCER SCREENING METHOD

(75) Inventors: Young-Ki Paik, Seoul (KR); Keun Na, Seoul (KR)

(73) Assignee: Industry-Academic Cooperation Foundation, Yonsei University, Seoul (KR)

( * ) Notice: Subject to any disclaimer, the term of this patent is extended or adjusted under 35 U.S.C. 154(b) by 0 days.

(21) Appl. No.: 12/994,406

(22) PCT Filed: Oct. 1, 2008

(86) PCT No.: PCT/KR2008/005762
§ 371 (c)(1),
(2), (4) Date: Nov. 23, 2010

(87) PCT Pub. No.: WO2009/113758
PCT Pub. Date: Sep. 17, 2009

(65) Prior Publication Data
US 2011/0097738 A1 Apr. 28, 2011

(30) Foreign Application Priority Data
Mar. 14, 2008 (KR) .................. 10-2008-0023707

(51) Int. Cl.
*G01N 33/573* (2006.01)
*C12Q 1/44* (2006.01)
(52) U.S. Cl. ......................................... 435/7.4; 435/19
(58) Field of Classification Search ............... 435/7.4; 536/23.2
See application file for complete search history.

(56) References Cited

U.S. PATENT DOCUMENTS
6,800,483 B1 10/2004 Danks et al.
7,906,637 B2 * 3/2011 Potter et al. .................. 536/23.2

FOREIGN PATENT DOCUMENTS
WO WO 02/02760 A2 1/2002
WO WO 02/06454 A2 1/2002

OTHER PUBLICATIONS

Guemei et al., "Human plasma carboxylesterase and butyrylcholinesterase enzyme activity: correlations with SN-38 pharmacokinetics during a prolonged infusion of irinotecan", In: Cancer Chemotherapy Pharmacology, vol. 47, No. 4, 2001, pp. 283-290.
International Search Report for PCT/KR2008/005762 dated Feb. 26, 2009.
Sanghani et al., "Carboxylesterases Expressed in Human Colon Tumor Tissue and Their Role in CPT-11 Hydrolysis", In: Clinical Cancer Research, vol. 9, No. 13, Oct. 15, 2003, pp. 4983-4991.

* cited by examiner

*Primary Examiner* — Peter J Reddig
*Assistant Examiner* — Yan Xiao
(74) *Attorney, Agent, or Firm* — Birch, Stewart, Kolasch & Birch, LLP

(57) ABSTRACT

The present invention relates to a plasma biomarker for diagnosing hepatocellular carcinoma (HCC), in particular to the discovery of a protein in plasma using 2-D fluorescence differential gel electrophoresis (2-D DIGE), immunoprecipitation and Nano-liquid chromatography mass spectrometry (Nano-LC-MS/MS) system that was unknown on the basis of conventional techniques. By demonstrating the presence of liver carboxylesterase 1 (hCE1) in human plasma and confirming that its secretion level is higher in patients with HCC than in healthy volunteers, this invention may be used as a screening method to diagnose HCC at an early stage.

3 Claims, 6 Drawing Sheets

[Figure 1]
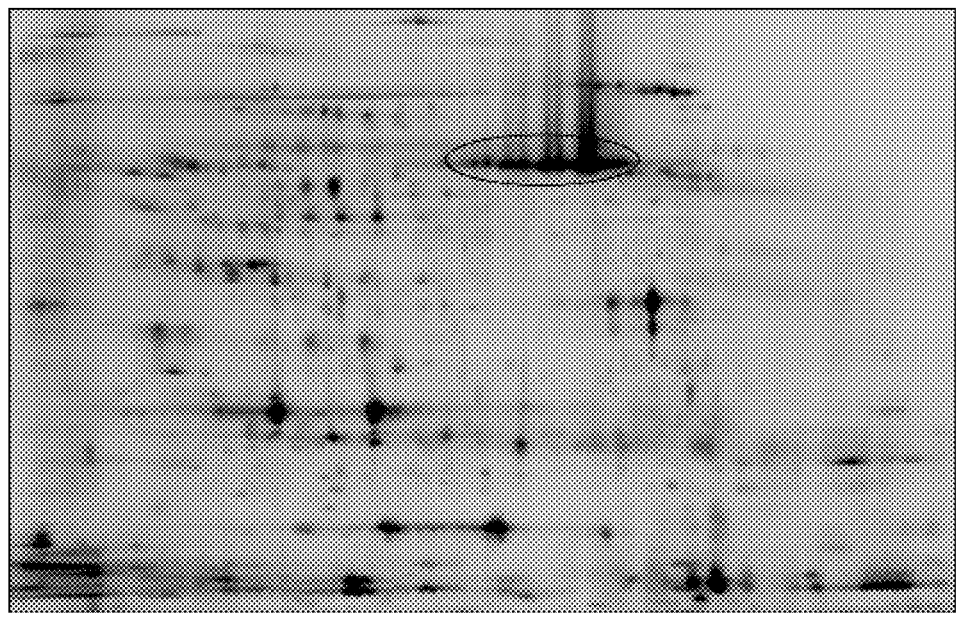
[Figure 2]
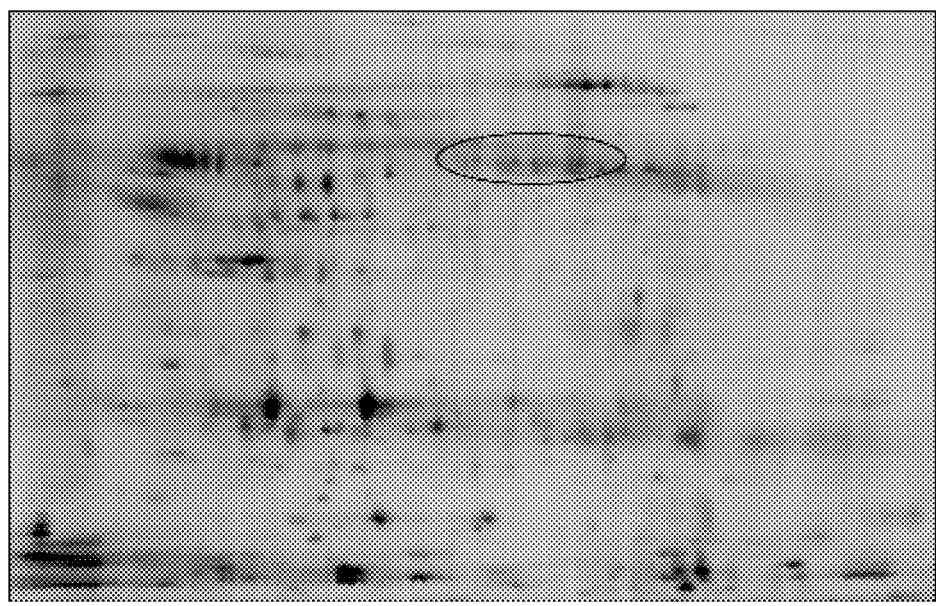

[Figure 3]
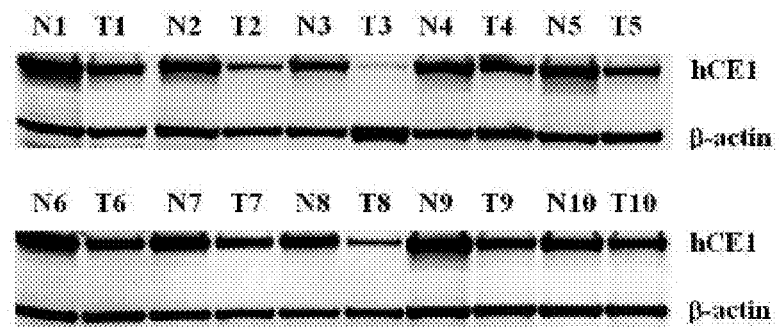
[Figure 4]
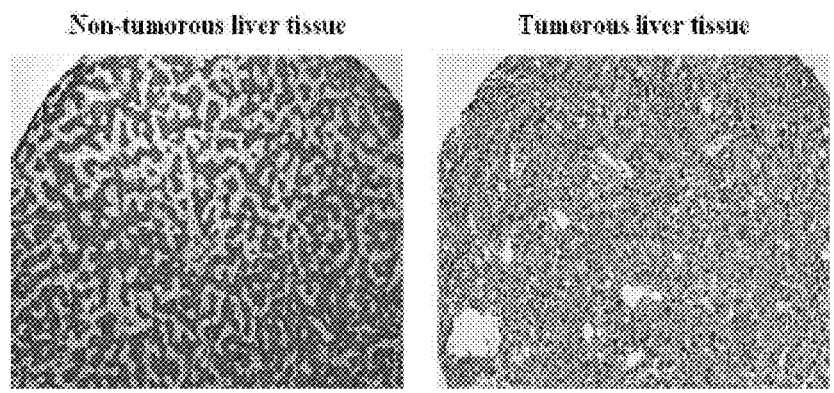
[Figure 5]
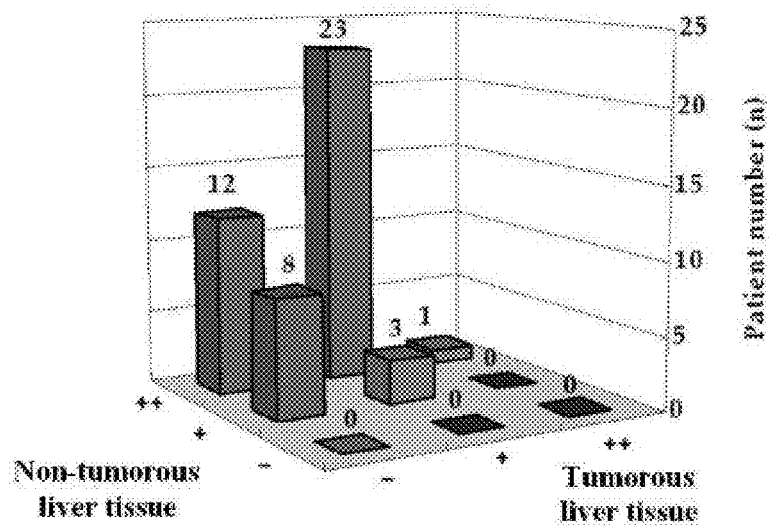

| Plasma fraction | Detected unique peptides | MH+ | DeltaCn | XC | Expect | Matched peptide sequence | SEQ ID NO |
|---|---|---|---|---|---|---|---|
| Healthy volunteer | 5 | 630.7860 | -0.8394 | 39 | 0.072 | K.FLSLDLQGDPR.E | 1 |
| | | 718.8540 | -0.8820 | 62 | 0.00034 | R.GNWGHLDQVAALR.W | 2 |
| | | 738.0840 | 0.4415 | 69 | 6.8e-05 | R.AISESGVAL TSVLVK.K | 3 |
| | | 781.9225 | 0.0995 | 58 | 0.00077 | R.QKTEEELLETTLK.M | 4 |
| | | 797.4555 | 1.1746 | 45 | 0.017 | K.EGYLQIGANTQAAQK.L | 5 |
| Patient with HCC | 14 | 456.5835 | 0.1340 | 41 | 0.034 | K.FWANFAR.N | 6 |
| | | 483.6755 | 0.1678 | 66 | 0.00012 | K.TAMSLLWK.S | 7 |
| | | 516.0580 | 0.9583 | 26 | 1.1 | K.ELIPEATEK.Y | 8 |
| | | 537.0990 | 0.0553 | 69 | 6.1e-05 | K. TPEELQAER.N | 9 |
| | | 631.1680 | -0.0754 | 75 | 1.3e-05 | K.FLSLDLQGDPR.E | 10 |
| | | 674.7735 | -0.9728 | 50 | 0.0042 | K.AGQLLSELFTNR.K | 11 |
| | | 480.1416 | 0.8270 | 45 | 0.012 | R.GNWGHLDQVAALR.W | 12 |
| | | 737.2790 | -1.1685 | 47 | 0.0079 | R.AISESGVAL TSVLVK.K | 13 |
| | | 497.8556 | -0.1135 | 24 | 1.5 | K.AVEKPPQTEHIEL.- | 14 |
| | | 508.0096 | 1.2395 | 58 | 0.00056 | R.N FH TVPYMVGIN K. Q | 15 |
| | | 781.5885 | -0.5685 | 66 | 9.2e-05 | R.QKTEEELLETTLK.M | 16 |
| | | 796.6530 | -0.4304 | 90 | 3.5e-07 | K.EGYLQIGANTQAAQK.L | 17 |
| | | 816.8500 | 0.8446 | 51 | 0.0032 | R.FTPPQPAEPWSFVK.N | 18 |
| | | 684.3526 | -1.1007 | 29 | 0.42 | R.NGNPNGEGLPHWPEYNQK.E | 19 |

| Plasma fraction | Detected unique peptides | MH+ | DeltaCn | XC | Expect | Matched peptide sequence |
|---|---|---|---|---|---|---|
| Health volunteer | 5 | 830.7806 | -0.8394 | 39 | 0.072 | K.FLSLDLQGDPR.E |
| | | 718.8540 | -0.8820 | 62 | 0.00034 | R.GNWGHLDQVAALR.W |
| | | 738.0846 | 0.4415 | 69 | 6.8e-05 | R.AISESQVALTSVLVR.K |
| | | 781.9225 | 0.0993 | 58 | 0.00077 | R.QKTEEELLETTLR.M |
| | | 797.4553 | 1.1786 | 43 | 0.017 | K.RGYLQRANTQAAQK.L |
| Patient with RCC | 14 | 456.3835 | 0.1340 | 41 | 0.034 | K.FWANFAR.N |
| | | 483.6755 | 0.1678 | 66 | 0.00012 | K.TAMSLLWK.S |
| | | 516.0388 | 0.9583 | 26 | 1.1 | K.RLIPEATEK.Y |
| | | 537.0990 | 0.0553 | 60 | 6.1e-05 | K.TPEELQAER.N |
| | | 631.1689 | -0.0754 | 75 | 1.3e-05 | K.FLSLDLQGDPR.E |
| | | 674.7755 | -0.2723 | 50 | 0.0042 | K.AGQLLSLFTNR.E |
| | | 480.1416 | 0.8270 | 45 | 0.012 | R.GNWGHLDQVAALR.W |
| | | 737.2799 | -1.1085 | 47 | 0.0079 | R.AISESQVALTSVLVR.K |
| | | 492.8556 | -0.1133 | 24 | 1.5 | K.AVEEPPQTEEHEL.- |
| | | 508.0096 | 1.2393 | 58 | 0.00086 | R.NPHTVPYMVGINK.Q |
| | | 781.5885 | -0.5885 | 66 | 9.2e-05 | R.QKTEEELLETTLR.M |
| | | 798.6530 | -0.4384 | 80 | 3.5e-07 | K.RGYLQRANTQAAQK.L |
| | | 816.8506 | 0.8486 | 51 | 0.0032 | R.FTPPQPAEPWSFVR.N |
| | | 684.3526 | -1.1007 | 29 | 0.42 | R.NGRNPNGEGLPDWFFYNQK.E |

[Figure 7]

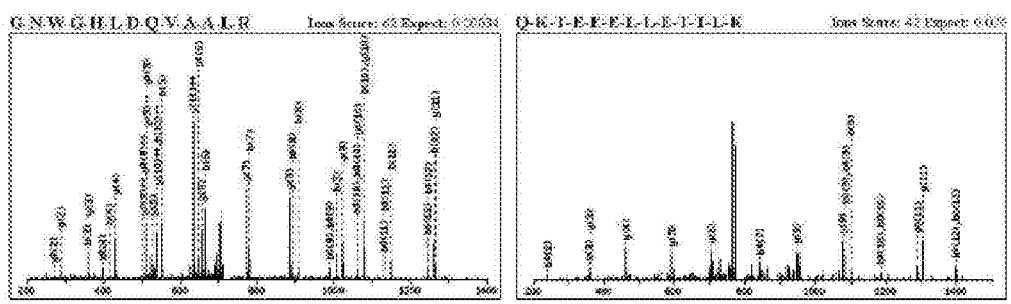

[Figure 8]

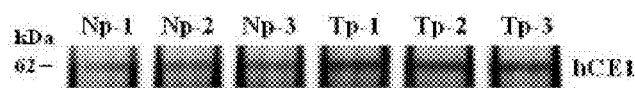

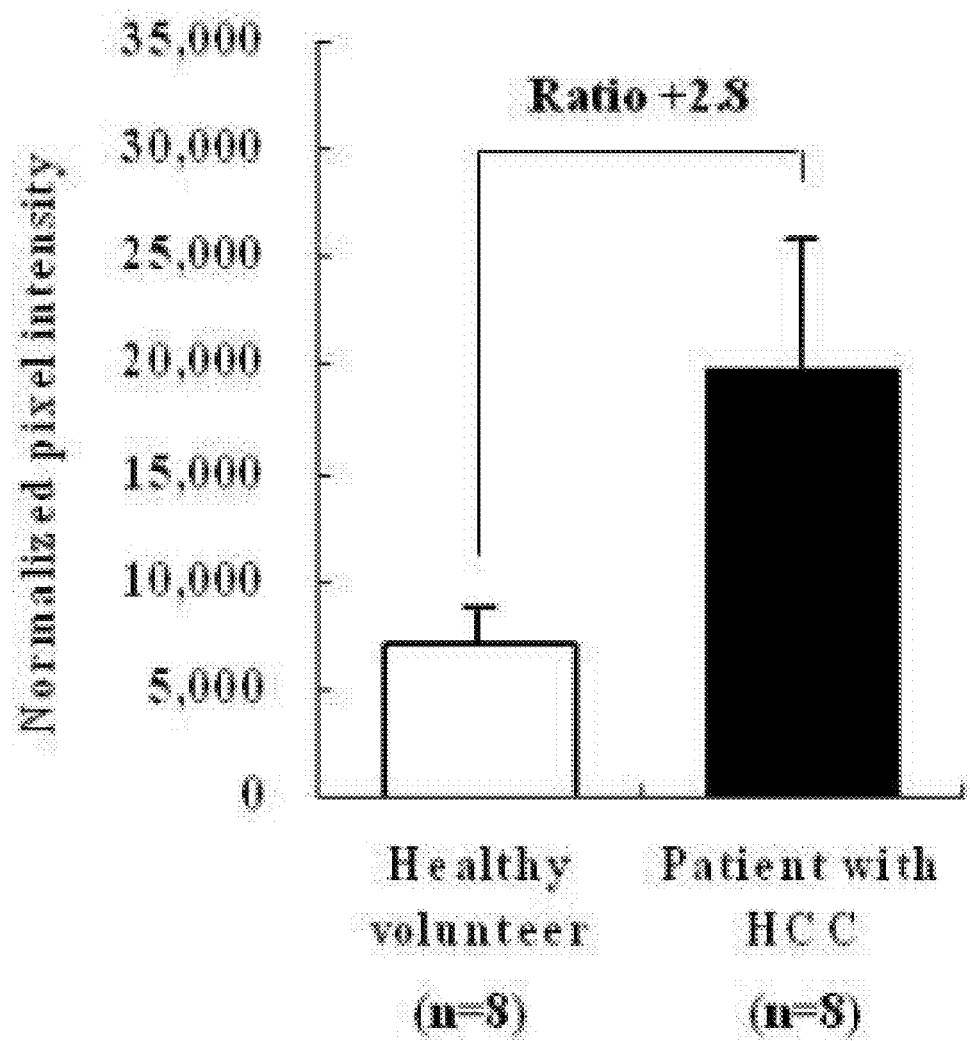
[Figure 9]

PLASMA BIOMARKER TOOL FOR THE DIAGNOSIS OF LIVER CANCER COMPRISING LIVER CARBOXYLESTERASE 1 AND LIVER CANCER SCREENING METHOD

TECHNICAL FIELD

The present invention pertains to a plasma biomarker (carboxylesterase 1) for the diagnosis of liver cancer (hepatocellular carcinoma; HCC), and the associated screening method for determining differential biomarker expression between healthy volunteers and patients with HCC employing 2-dimensional fluorescence gel electrophoresis (2-D DIGE), immunoprecipitation and nano liquid chromatography mass spectrometry (Nano-LC-MS/MS) system. The amount of biomarker protein secreted into plasma is measured and used as an indicator of the presence of HCC.

BACKGROUND ART

Hepatocellular carcinoma (HCC) is the fifth most common cancer worldwide and has the fourth highest mortality rate. It is an especially major problem among Asian and African populations. Unlikely patients with other cancers, such as lung cancer and breast cancers, more than 95% of HCC patients die within five years of being diagnosed with HCC.

Although HCC is the subject of continuing investigation and its symptoms are well known, early-stage diagnosis of this disease remains difficult and the survival rate after diagnosis is very low (3%-5%).

In addition to tissue biopsies, which are used for diagnosing HCC by computed tomography (CT) and magnetic resonance imaging (MRI), bodily fluids, such as plasma, provide a clinical sample that allows for the simultaneous measurement of proteins to determine the possible presence of HCC.

To date, the biomarkers alpha-fetoprotein (AFP), des-gamma-carboxyprothrombin (DCP), glypican-3 (GPC3), alpha-1-fucosidase and transforming growth factor-b1 have been used, alone or in combination, for the clinical screening of HCC patients. Although these biomarkers are useful for the detection of HCC, they suffer from poor sensitivity and/or specificity. For example, alpha-fetoprotein, which has been used as a serum marker for HCC for many years, has low sensitivity (39%-65%) and moderate specificity (76%-94%). Thus, there is an urgent need for a new class of biomarkers with enhanced sensitivity and specificity, and which are capable of diagnosing HCC at an early stage.

The inventors of the present invention have discovered an N-linked glycosylated protein that is a specific biomarker for HCC. This protein, human liver carboxylesterase 1 (hCE1), was identified by 2-dimensional gel electrophoresis (2-D DIGE) and nano-liquid chromatography mass spectrometry (Nano-LC-MS), and found to be differentially expressed in clinical plasma samples obtained from healthy volunteers and HCC patients.

The candidate HCC biomarker protein, hCE1, which is expressed mainly in the liver, is known to be expressed at lower levels in HCC tissues relative to normal liver tissue. However, there are no reports on the direct detection of secreted hCE1 protein in human bodily fluid (i.e., plasma). Consistent with this, searches of the public plasma protein database (www.plasmaproteomedatabase.org) by the inventors have failed to uncover evidence for hCE1 in plasma.

Previous studies related to hCE1 in human plasma have used enzymatic assays employing the non-specific substrates, triolein or p-nitrophenyl acetate, to measure the activity of hCE1 or its isoforms in samples purified by sepharose-affinity chromatography. However, it has recently been reported that this hydrolytic activity is likely attributable to the esterase activity of butyrylcholinesterase, paraoxonase and albumin, which are also present in human plasma. This interpretation is supported by the observation that the specific hCE1 inhibitor, bis-p-nitrophenylphosphate (BNPP), failed to confirm the presence of hCE1 in human plasma.

In this context, the inventors have used proteomics techniques to detect hCE1 in both liver tissue and plasma. Using immunoprecipitation and the proteomics techniques, 2-D DIGE and Nano-LC-MS/MS system, the inventors have demonstrated that hCE1 is present in the plasma of both healthy volunteers and patients with HCC, and provided evidence that hCE1 represents a novel HCC biomarker.

DISCLOSURE OF INVENTION

Technical Problem

The object of the present invention is to provide new evidence that hCE1 is a diagnostic biomarker for HCC that can effectively detect the presence of HCC using patient plasma and a routine detection method.

The HCC screening method provided by the present invention comprises the steps necessary to confirm the presence of hCE1 in a human blood sample, and discriminate between an patient with HCC and a healthy volunteer through quantitative measurement of hCE1 in plasma using immunoprecipitation, Western blot analysis and Nano-LC-MS/MS system.

Technical Solution

To achieve the above objective, the present invention verifies using 2-D DIGE and Western blot analysis that hCE1 expression is remarkably reduced in tumorous liver tissue compared to non-tumorous liver tissue of a patient with HCC.

The present invention also uses proteomic techniques (Nano-LC-MS/MS system) to establish that hCE1 is, in fact, a plasma protein, something that had not been previously shown using conventional methods. Furthermore, the present invention shows that the level of hCE1 protein is 2-5 fold higher, on average, in the plasma of patients with HCC than in that of healthy volunteers.

Because hCE1 is an N-linked glycoprotein, which binds lectin, the present invention employed lectin-affinity chromatography for glycoprotein separation in the analysis of non-tumorous and tumorous liver tissue. This was followed by 2-D DIGE, which localized hCE1 protein to a position on the 2-D map that corresponded to a molecular weight of approximately 62 kDa and a PI of 4.5-5.3.

With the methods described in the present invention, the presence of hCE1 was validated using immunoprecipitation and a highly-sensitive Nano-LC-MS/MS-based method after enrichment on magnetic beads (Dynabeads, Invitrogen). During the course of establishing optimal Dynabeads-aliquot and plasma-concentration conditions, it was also determined that a comparative analysis of the levels of hCE1 in plasma from healthy volunteers and patients with HCC could be accomplished using Western blot analyses.

According to the present invention, the presence of hCE1 in human plasma can be confirmed through the use of proteomic technology by applying the following steps:

a) Collect a blood sample into a tube containing di-potassium ethylenediamine tetraacetic acid ($K_2$EDTA) and maintain for 30 minutes at roam temperature; centrifuge for 15 minutes at 2,400×g to obtain plasma (supernatant);

b) Combine 400 μg of anti-hCE1 antibody with 10 mg of magnetic beads, then transfer 500 μg of the antibody-coated magnetic beads to a 1 ml tube containing 8 mg plasma from HCC patients or healthy volunteers and incubate for 2 hours to immunoprecipitate hCE1 and separate it from the remaining plasma proteins;

c) Denature each sample of immunoprecipitated hCE1 from healthy volunteers and HCC patients in lysis buffer, and separate the samples using 1-dimensional gel electrophoresis;

d) Excise the gel band at approximately 62 kDa, and digest the protein into peptides using trypsin; and e) Analyze the peptide digest using high-sensitivity Nano-LC-MS/MS system to identify hCE1 protein (See FIG. 6 and FIG. 7).

Furthermore, the level of secreted hCE1 in human plasma is also measured in the present invention and can be used as a biomarker for discriminating between an patient with HCC and a healthy volunteer using the following series of steps:

1) Confirm that the level of hCE1 expression in tumorous liver tissue from a patient with HCC is markedly decreased compared to non-tumorous liver tissue using 2-D DIGE and Western blot analysis;

2) Immunoprecipitate a plasma sample as described above steps a-b) to obtain a solution of hCE1;

3) Confirm the presence of hCE1 signal by Western blotting analysis using an anti-hCE1 antibody; and 4) Verify that the hCE1 signal is stronger in the plasma of patients with HCC than in that of the healthy volunteers (See FIG. 8 and FIG. 9).

BRIEF DESCRIPTION OF THE DRAWINGS

FIG. 1 is a photograph showing a 2-D DIGE image of fractionated glycoproteins from non-tumorous liver tissue from a patient with HCC; the position of hCE1 is indicated.

FIG. 2 is a photograph showing a 2-D DIGE image of fractionated glycoproteins from tumorous liver tissue from a patient with HCC; the position of hCE1 is indicated.

FIG. 3 is a photograph showing the differences in hCE1 expression levels in paired samples of non-tumorous and tumorous liver tissue from additional ten patients with HCC.
N: Non-tumorous liver tissue
T: Tumorous liver tissue FIG. 4 is a photograph of an immunohistochemically stained, paraffin-embedded tissue array constructed from paired non-tumorous and tumorous liver sections from 47 patients with HCC showing the level of hCE1 expression.

FIG. 5 is a graph depicting the frequency distribution of staining scores determined by immunohistochemical staining in paired non-tumorous and tumorous liver sections of patients with HCC. The results indicate that the level of hCE1 expression is specifically reduced in the tumorous liver sections compared to the non-tumorous liver sections.

FIG. 6 is a table showing the tryptic peptides of hCE1 identified by Nano-LC-MS/MS system in the plasma of healthy volunteers and patients with HCC, and used to validate the presence of hCE1 in human plasma.

FIG. 8 is a photograph showing the differences in hCE1 levels between representative three healthy volunteers and three patients with HCC, determined using Western blot analysis after immunoprecipitation.
Np: plasma of healthy volunteer
Tp: plasma of patient with HCC FIG. 9 is a graph comparing the hCE1 levels in the plasma of eight healthy volunteers and eight patients with HCC.

BEST MODE FOR CARRYING OUT THE INVENTION

Figure 7:
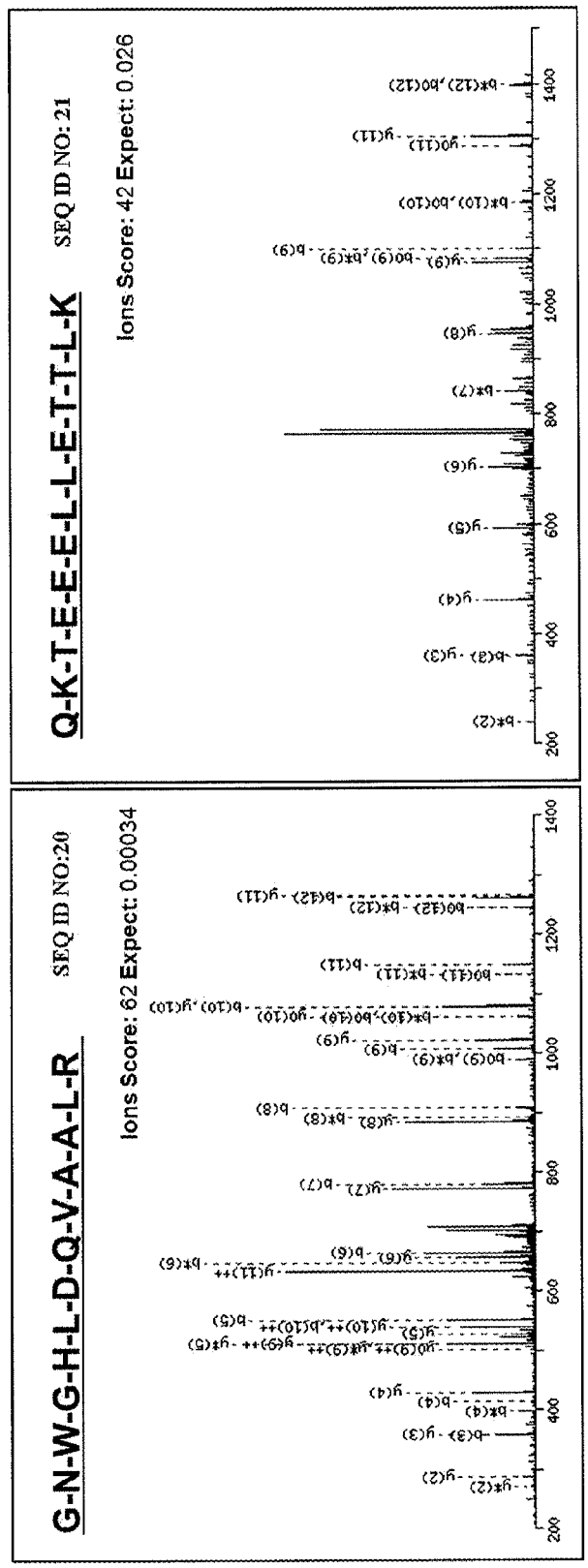
FIG. 7 is a representative Nano-LC-MS/MS chromatograph of the common peptides shown in FIG. 6.

The present invention is described in detail in the following embodiments. The embodiments are only included to describe the present invention, however, the scope of the present invention is not limited to the embodiments.

Embodiment 1: Collection of Clinical Tissues and Plasma

The non-tumorous and tumorous liver tissue from patients with HCC were obtained along with pathological individual information from the Department of Pathology, Yonsei University College of Medicine, Seoul, Korea. The following tests were used to assess the appropriateness of plasma from healthy volunteers to serve as a negative control: HIV-1 and HIV-2 antibodies derived from HIV, which is a liver-cancer indicating standard test element; HIV-1 antigen; hepatitis B surface antigen; hepatitis B core antigen; hepatitis C virus; T-Cell Leukemia Virus (HTLV-I/II) antigen; and Treponema pallidum. Plasma was obtained according to a standardized sample separation method formally adopted by the Human Proteome Organization (HUPO).

Each blood sample (4 ml) from man or woman was maintained in a tube containing di-potassium ethylenediamine tetraacetic acid ($K_2$EDTA) for 30 minutes at room temperature, followed by centrifugation for 15 minutes at 2,400×g. A supernatant (plasma) was retained. Samples of non-tumorous, tumorous liver tissue, and plasma were stored at −70° C. until ready for use. Liver tissues and plasma were acquired according to approved procedures of the Institutional Review Board (IRB) at Yonsei University College of Medicine with informed consent of the patients.

Embodiment 2: Separation of Glycoproteins in Non-Tumorous and Tumorous Liver Tissue A 100 mg sample of each tissue was homogenized in RIPA buffer (50 mM Tris, 150 mM NaCl, 1% Nonidet P-40, 0.25% sodium deoxycholate, pH 7.4) at 4° C. Glycoproteins were separated by lectin-affinity chromatography using a mixture of five different agarose-bound lectins: concanavalin A, wheat germ agglutinin, Jacalin, *Sambucus nigra,* and *Aleuria aurantia.* The lectin mixture, with binding specificities for glycoproteins with different sugar compositions, was packed into a 2 ml PD-10 column (Pierce). Glycoprotein-containing samples were applied to the column in binding buffer (20 mM Tris, 1 mM $MnCl_2$, 1 mM $CaCl_2$, 0.15 M NaCl, pH 7.4) and allowed to interact with the column for 30 minutes.

The bound glycoproteins were eluting with a buffer (0.2 M methyl-D-mannopyroside, 0.2 M methyl-D-glucopyroside, 0.2 M N-acetylglucosamine, 0.2 M galactose, 0.1 M lactose, 0.1 M fucose, 20 mM Tris, 0.5 M NaCl, pH 7.0) that displaces glycoproteins on the basis of sugar composition. The eluted glycoproteins were concentrated using a 5-kDa membrane filter, and precipitated with 50% trichloroacetic acid and 100% ice-cold acetone. The precipitate was dissolved in 2-D lysis buffer (7 M urea, 2 M thiourea, 4% CHAPS, 30 mM Tris, pH 8.5), and the resulting protein solution was adjusted to pH 8.5. The concentration of the protein was measured using a 2D Quant kit (GE Healthcare).

Embodiment 3: 2-Dimensional Fluorescence Differential Gel Electrophoresis (2-D DIGE)

Ten paired samples (five from non-tumorous liver tissue and five from tumorous liver tissue) from five patients were used to prepare analytic samples (50 μg each) for 2-D DIGE. Analytic samples and a corresponding pooled standard sample were labeled individually with the fluorescent dyes, Cy3, Cy5 and Cy2 (400 pmol; GE Healthcare) in the dark for 30 minutes.

The reaction was stopped by adding 1 µl 10 mM lysine, and the three labeled samples were mixed, adjusted to a final volume of 450 µl by adding sample buffer (6 M urea, 2 M thiourea, 4% CHAPS, 60 mM dithiothreitol (DTT), 30 mM Tris, pH 8.5) and rehydrated by incubating with a 2% IPG 3-10 NL buffer solution for 16 hours at room temperature.

Isoelectric focusing (IEF) was performed using the Immobiline DryStrip pH 3-10 NL under optimized conditions (up to 95,000 V) on the MultiPhor II electrophoresis system (GE Healthcare), followed by a one-step reduction and alkylation in which the DryStrip was incubated for 25 minutes in a tributylphosphine (TBP) buffer solution (6 M urea, 2% sodium dodecyl sulfate [SDS], 30 mM Tris, 20% glycerol, 2.5% acrylamide solution, 5 mM TBP).

After reduction and alkylation, the isoelectrically focused proteins were separated in the second dimension by electrophoresis on 9%-16% gradient polyacrylamide gels using an Ettan Dalt-twelve electrophoresis system (GE Healthcare). Each gel was then scanned at wavelengths corresponding to Cy2, Cy3 and Cy5 using a Typhoon 9400 (GE Healthcare) scanner, and images of each gel were analyzed using Decyder 2-D analysis software (GE Healthcare).

Embodiment 4: Identification of 2-D DIGE-Separated Proteins

After images were analyzed, a spot corresponding to a significantly differentially expressed protein was excised from a Coomassie blue-stained gel, destained and digested with trypsin. The digested peptides were desalted using a Poros R2 and Oligo R3 resin mixture. The protein was analyzed using a 4800 MALDI-TOF-MS (Applied Biosystem) and the spectra were identified using a MASCOT database.

Embodiment 5: Validation of HCC Biomarker Expression Levels in Tissues by Western Blot Analysis Differences in HCC biomarker protein concentration between non-tumorous and tumorous liver tissue from ten patients were verified by Western blotting analysis. An equal amount of protein (5 µg) from each sample was separated by SDS-PAGE on 10% gels.

Proteins were then transferred to a nitrocellulose (NC) membrane, and blocked by incubating in TBS-T buffer (20 mM Tris, 137 mM NaCl, 0.1% Tween-20, pH 7.6) containing 5% skim milk for 1 hour at roam temperature. Membranes were then incubated with primary anti-hCE1 antibody (CE1, Abcam; 1:10000 in TBS-T/5% skim milk) for 1 hour at room temperature. A mouse β-actin antibody (Santa Cruz) was used as a positive control.

After washing with TBS-T/5% skim milk, membranes were incubated with secondary horseradish peroxidase (HRP)-conjugated anti-rabbit IgG (Santa Cruz; 1:20000 dilution) for 1 hour at room temperature. Immunoreactive proteins were detected using ECL Plus Western blot reagents (GE Healthcare), and blots were scanned and analyzed using a Typhoon 9400 scanner.

Embodiment 6: Validation of HCC Biomarker Expression Levels in Tissues Using an Immunohistochemical Staining Method Paraffin-embedded tissue arrays constructed from paired tissues from non-tumorous and tumorous liver sections of 47 patients with HCC were used for immunohistochemistry. The slides were deparaffinized with xylene and alcohol, hydrated, and then treated with 0.6% hydrogen peroxide. Anti-hCE1 antibody (1:100) was applied to the slide and incubated for 30 minutes. hCE1-bound antibody color was developed using ChemMate Envision Kit (DAKO) and colorized with hematoxylin (used as a contrast staining agent) for 30 seconds. The intensity of staining was scored as 1) "−", for no staining; 2) "+", for weak staining; and 3) "++", for strong staining.

Embodiment 7: Validation of HCC Biomarker Protein Secretion Level in Human Plasma by Immunoprecipitation and Western Blot Analysis Dynabead MyOne™ Tosylactivated (Invitrogen) magnetic beads were coated with anti-hCE1 antibody as described by the manufacturer. Briefly, magnetic beads (10 mg) and anti-hCE1 antibody (400 µg) were mixed and incubated for 16 hours in binding buffer (0.1 M sodium borate, 1 M ammonium sulfate, pH 9.5) at 37° C., and then blocked with TBS-T/5% skim milk for an additional 16 hours. hCE1 was immunoprecipitated from the plasma of healthy volunteers and patients with HCC by transferring antibody-coated beads (500 µg) to 1 ml tubes containing 8 mg plasma and incubating for 2 hours.

Antibody-bound proteins were eluted by adjusting the pH of the TBS-T buffer to pH 2. Differences in hCE1 levels between the plasmas of healthy volunteers and patients with HCC were determined by Western blot analysis using a primary anti-hCE1 antibody (Abcam; 1:1000) and a secondary anti-rabbit IgG-HRP antibody (Santa Cruz; 1:5000), as described in Embodiment 5.

Embodiment 8: Validation of hCE1 Protein in Human plasma by Nano-LC-MS/MS System A band corresponding to hCE1 based on Western blot analysis (embodiment 7) was excised from the gel, and reduced and alkylated by dithiothrietol(DTT)/iodoacetic acid (IAA) treatment. After digesting with trypsin to yield peptides, the identity of the gel-isolated protein as hCE1 was validated using Nano-LC-MS/MS system and a linear trap quadrupole (LTQ) detector.

INDUSTRIAL APPLICABILITY

As described above, hCE1 was discovered as a new biomarker for HCC diagnosis. According to the present invention, hCE1 protein secretion level in plasma can function as an index that allows early diagnosis of HCC, and thereby contributes to increasing the survival rate among patients with HCC by enabling timely therapeutic intervention.

The invention claimed is:
1. A screening method for hepatocellular carcinoma (HCC), comprising:
    collecting human blood, and
    detecting the presence of human liver carboxylesterase 1(hCE1) protein in plasma of the human blood as a plasma biomarker for HCC diagnosis; wherein the level of hCE1 protein is increased more in the plasma of patients with HCC than in the plasma of healthy patients.

2. The method of claim 1, wherein the level of hCE1 protein is increased, on average, 2-5 fold more in the plasma of patients with HCC compared to the plasma of healthy patients.

3. The method of claim 1, wherein the presence of the hCE1 protein is detected by an anti-hCE1 antibody.

* * * * *

SEQUENCE LISTING

<160> NUMBER OF SEQ ID NOS: 21

<210> SEQ ID NO 1
<211> LENGTH: 13
<212> TYPE: PRT
<213> ORGANISM: Homo sapiens

<400> SEQUENCE: 1

Lys Phe Leu Ser Leu Asp Leu Gln Gly Asp Pro Arg Glu
1               5                   10

<210> SEQ ID NO 2
<211> LENGTH: 15
<212> TYPE: PRT
<213> ORGANISM: Homo sapiens

<400> SEQUENCE: 2

Arg Gly Asn Trp Gly His Leu Asp Gln Val Ala Ala Leu Arg Trp
1               5                   10                  15

<210> SEQ ID NO 3
<211> LENGTH: 17
<212> TYPE: PRT
<213> ORGANISM: Homo sapiens

<400> SEQUENCE: 3

Arg Ala Ile Ser Glu Ser Gly Val Ala Leu Thr Ser Val Leu Val Lys
1               5                   10                  15

Lys

<210> SEQ ID NO 4
<211> LENGTH: 15
<212> TYPE: PRT
<213> ORGANISM: Homo sapiens

<400> SEQUENCE: 4

Arg Gln Lys Thr Glu Glu Glu Leu Leu Glu Thr Thr Leu Lys Met
1               5                   10                  15

<210> SEQ ID NO 5
<211> LENGTH: 17
<212> TYPE: PRT
<213> ORGANISM: Homo sapiens

<400> SEQUENCE: 5

Lys Glu Gly Tyr Leu Gln Ile Gly Ala Asn Thr Gln Ala Ala Gln Lys
1               5                   10                  15

Leu

<210> SEQ ID NO 6
<211> LENGTH: 9
<212> TYPE: PRT
<213> ORGANISM: Homo sapiens

<400> SEQUENCE: 6

Lys Phe Trp Ala Asn Phe Ala Arg Asn
1               5

<210> SEQ ID NO 7
<211> LENGTH: 10
<212> TYPE: PRT
<213> ORGANISM: Homo sapiens

<400> SEQUENCE: 7

Lys Thr Ala Met Ser Leu Leu Trp Lys Ser
1               5                   10

<210> SEQ ID NO 8
<211> LENGTH: 11
<212> TYPE: PRT
<213> ORGANISM: Homo sapiens

```
<400> SEQUENCE: 8

Lys Glu Leu Leu Pro Glu Ala Thr Glu Lys Tyr
1               5                   10

<210> SEQ ID NO 9
<211> LENGTH: 11
<212> TYPE: PRT
<213> ORGANISM: Homo sapiens

<400> SEQUENCE: 9

Lys Thr Pro Glu Glu Leu Gln Ala Glu Arg Asn
1               5                   10

<210> SEQ ID NO 10
<211> LENGTH: 13
<212> TYPE: PRT
<213> ORGANISM: Homo sapiens

<400> SEQUENCE: 10

Lys Phe Leu Ser Leu Asp Leu Gln Gly Asp Pro Arg Glu
1               5                   10

<210> SEQ ID NO 11
<211> LENGTH: 14
<212> TYPE: PRT
<213> ORGANISM: Homo sapiens

<400> SEQUENCE: 11

Lys Ala Gly Gln Leu Leu Ser Glu Leu Phe Thr Asn Arg Lys
1               5                   10

<210> SEQ ID NO 12
<211> LENGTH: 15
<212> TYPE: PRT
<213> ORGANISM: Homo sapiens

<400> SEQUENCE: 12

Arg Gly Asn Trp Gly His Leu Asp Gln Val Ala Ala Leu Arg Trp
1               5                   10                  15

<210> SEQ ID NO 13
<211> LENGTH: 17
<212> TYPE: PRT
<213> ORGANISM: Homo sapiens

<400> SEQUENCE: 13

Arg Ala Ile Ser Glu Ser Gly Val Ala Leu Thr Ser Val Leu Val Lys
1               5                   10                  15
Lys

<210> SEQ ID NO 14
<211> LENGTH: 14
<212> TYPE: PRT
<213> ORGANISM: Homo sapiens

<400> SEQUENCE: 14

Lys Ala Val Glu Lys Pro Pro Gln Thr Glu His Ile Glu Leu
1               5                   10

<210> SEQ ID NO 15
<211> LENGTH: 15
<212> TYPE: PRT
<213> ORGANISM: Homo sapiens

<400> SEQUENCE: 15
```

```
Arg Asn Phe His Thr Val Pro Tyr Met Val Gly Ile Asn Lys Gln
1               5                   10                  15
```

<210> SEQ ID NO 16
<211> LENGTH: 15
<212> TYPE: PRT
<213> ORGANISM: Homo sapiens

<400> SEQUENCE: 16

```
Arg Gln Lys Thr Glu Glu Glu Leu Leu Glu Thr Thr Leu Lys Met
1               5                   10                  15
```

<210> SEQ ID NO 17
<211> LENGTH: 17
<212> TYPE: PRT
<213> ORGANISM: Homo sapiens

<400> SEQUENCE: 17

```
Lys Glu Gly Tyr Leu Gln Ile Gly Ala Asn Thr Gln Ala Ala Gln Lys
1               5                   10                  15

Leu
```

<210> SEQ ID NO 18
<211> LENGTH: 16
<212> TYPE: PRT
<213> ORGANISM: Homo sapiens

<400> SEQUENCE: 18

```
Arg Phe Thr Pro Pro Gln Pro Ala Glu Pro Trp Ser Phe Val Lys Asn
1               5                   10                  15
```

<210> SEQ ID NO 19
<211> LENGTH: 20
<212> TYPE: PRT
<213> ORGANISM: Homo sapiens

<400> SEQUENCE: 19

```
Arg Asn Gly Asn Pro Asn Gly Glu Gly Leu Pro His Trp Pro Glu Tyr
1               5                   10                  15

Asn Gln Lys Glu
            20
```

<210> SEQ ID NO 20
<211> LENGTH: 13
<212> TYPE: PRT
<213> ORGANISM: Homo sapiens

<400> SEQUENCE: 20

```
Gly Asn Trp Gly His Leu Asp Gln Val Ala Ala Leu Arg
1               5                   10
```

<210> SEQ ID NO 21
<211> LENGTH: 13
<212> TYPE: PRT
<213> ORGANISM: Homo sapiens

<400> SEQUENCE: 21

```
Gln Lys Thr Glu Glu Glu Leu Leu Glu Thr Thr Leu Lys
1               5                   10
```